United States Patent [19]
Costantini et al.

[11] Patent Number: 5,003,114
[45] Date of Patent: Mar. 26, 1991

[54] HYDROXYLATION OF PHENOLS/PHENOL ETHERS

[75] Inventors: Michel Costantini; Michel Gubelmann; Jean-Pierre Lecomte, all of Lyons; Jean-Michel Popa, Drancy, all of France

[73] Assignee: Rhone-Poulenc Chimie, Courbevoie, France

[21] Appl. No.: 362,584

[22] Filed: Jun. 7, 1989

[30] Foreign Application Priority Data

Jun. 8, 1988 [FR] France .................................. 88 07882

[51] Int. Cl.$^5$ ............................................. C07C 37/60
[52] U.S. Cl. .................................... 568/771; 568/741; 568/800; 568/803
[58] Field of Search ............... 568/629, 771, 803, 754, 568/860, 902, 768, 741

[56] References Cited

U.S. PATENT DOCUMENTS 4,394,300 7/1983 Chu et al. ............................. 502/77

FOREIGN PATENT DOCUMENTS 2083816 3/1982 United Kingdom .

OTHER PUBLICATIONS

Nature, vol. 272, Mar. 30, 1978, "Structure of Synthetic Zeolite ZSM-5", pp. 2 and 3, G. T. Kokotailo et al.
Zeolites, 1986, vol. 6, Jul.; "Effect of the Aluminium Content on the ZSM-5 Zeolite Crystallization in the Presence of Alkanolamine", pp. 312–316.

Primary Examiner—Werren B. Lone
Attorney, Agent, or Firm—Burns, Doane, Swecker & Mathis

[57] ABSTRACT

Phenols/phenol ethers are hydroxylated by reaction with hydrogen peroxide in the presence of a catalytically effective amount of a calcined germanozeosilite MFI zeolite.

30 Claims, No Drawings

HYDROXYLATION OF PHENOLS/PHENOL ETHERS

BACKGROUND OF THE INVENTION

1. Field of the Invention

The present invention relates to the hydroxylation of phenols or phenol ethers, and, more especially, to the hydroxylation of phenols or phenol ethers by reacting such starting compounds with hydrogen peroxide in the presence of a germanozeosilite MFI zeolite.

2. Description of the Prior Art

The hydroxylation of phenol or of substituted phenols using hydrogen peroxide, to prepare diphenols, is known to this art.

French Patent No. 69/45,467, published under No. 2,071,464, describes such a process in which the reaction is catalyzed by a strong acid, for example perchloric acid or sulfuric acid.

German Patent No. 2,410,742 describes a process similar to that of the '467 French patent, in which the hydrogen peroxide is employed in the form of an essentially anhydrous organic solution.

The above prior art processes are of considerable interest and the former is carried out industrially.

However, for a number of years attempts have been made to catalyze the hydroxylation reaction using solids which are not dissolved in the reaction mixture, in order to simplify their separation from the reaction mixture to permit their optional recycling and to avoid the saline by-products which are typically formed during the step of removal of the dissolved acidic catalysts.

French Patent Application No. 81/17,023 (published under No. 2,489,816) thus describes the use of titanium silicalite as a heterogeneous catalyst for the hydroxylation of aromatic compounds with hydrogen peroxide.

The fine size of the catalyst particles employed makes their separation from the reaction mixture very difficult and their recycling problematic, whereas, in an industrial process, it is essential that a costly catalyst be recycled.

To overcome this problem of catalyst separation, it has been proposed, in the European Patent Application published under No. 200,260, to employ agglomerates of such finely divided particles of titanium silicalite.

Nonetheless, serious need continues to exist in this art for more effective heterogeneous catalysis of the hydroxylation of phenols or phenol ethers using hydrogen peroxide.

SUMMARY OF THE INVENTION

Accordingly, a major object of the present invention is the provision of an improved process for heterogeneously catalyzing the hydroxylation of phenols and phenol ethers by means of hydrogen peroxide, and which improved process can be carried out on an industrial scale under economically attractive conditions.

Briefly, the present invention features a process for the hydroxylation of phenols or phenol ethers, comprising reacting a compound having the formula (I):

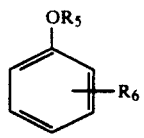

(I)

in which $R_5$ is a hydrogen atom, or a methyl, ethyl or phenyl radical, and $R_6$ is a hydrogen atom, an alkyl radical having from 1 to 4 carbon atoms, an alkoxy radical having from 1 to 4 carbon atoms, or a phenyl or cyclohexyl radical; with hydrogen peroxide, in the presence of a catalytically effective amount of a zeolite of MFI structure based on silicon oxide and germanium oxide and having, after calcination, the following formula (II):

$$Si_{(96-x)} \cdot Ge_x O_{192} \qquad (II)$$

wherein x ranges from about 0.1 to 36.

DETAILED DESCRIPTION OF THE PREFERRED EMBODIMENTS OF THE INVENTION

More particularly according to the present invention, the subject zeolites are hereby designated "germanozeosilites".

The germanozeosilite employed in the process of the invention has a monoclinic crystalline system and shows an X-ray diffraction pattern as set forth in the following Table.

The extreme values of the various lattice constant distances $d_{hkl}$ are reported in this Table and correspond to the limiting concentrations of germanium incorporated into the zeolite structure, or, more precisely, to the Ge/(Si+Ge) ratio.

In point of fact, the identification of germanozeosilites can be particularly and advantageously established by their X-ray diffraction pattern.

This diffraction pattern may be obtained using a diffractometer by employing the conventional powder method with copper $K\alpha$ radiation. The lattice constant distances $d_{hkl}$ characterizing the sample are calculated, using the Bragg relationship, from the position of the diffraction peaks, represented by the angle $2\theta$. The estimate of the measurement error $\Delta(d_{hkl})$ of $d_{hkl}$ is calculated, as a function of the absolute error $\Delta(2\theta)$ associated with the measurement of $2\theta$, using the Bragg relationship. An absolute error $\Delta(2\theta)$ equal to $\pm 0.2°$ is commonly accepted. The relative intensity $I/I_o$ associated with each value of $d_{hkl}$ is estimated from the height of the corresponding diffraction peak. A scale of symbols is frequently employed to characterize this intensity: SS=very strong, S=strong, mS=medium to strong, m=medium, mw=medium to weak, w=weak, ww=very weak.

The value of the volume $V_o$ of the crystal lattice of germanozeosilites is a function of the substitution of silicon by germanium.

In another embodiment, the germanozeosilites employed in the invention may contain fluorine when $F^{31}$ anions have been employed as a mobilizer. The fluorine concentration generally ranges from 0.01 to 1.4% by weight after calcination. Such fluorine values may, however, be removed by a hydrothermal treatment at pH>7 without, nevertheless, modifying the structure of the germanozeosilite of the invention.

TABLE

| X-ray diffraction pattern | | | |
|---|---|---|---|
| Extreme values of $d_{hkl}$ (nm) | $I/I_o$ | Extreme values of $d_{hkl}$ (nm) | $I/I_o$ |
| 1.120–1.123 | S-SS | 0.460–0.464 | w |
| 0.992–1.004 | S-SS | 0.444–0.449 | w |
| 0.973–0.984 | w | 0.434–0.439 | w |
| 0.896–0.904 | ww | 0.422–0.427 | w |

TABLE-continued

| X-ray diffraction pattern | | | |
|---|---|---|---|
| Extreme values of $d_{hkl}$ (nm) | $I/I_o$ | Extreme values of $d_{hkl}$ (nm) | $I/I_o$ |
| 0.803–0.811 | ww | 0.406–0.411 | ww |
| 0.742–0.750 | ww (broad) | 0.400–0.403 | w |
| 0.705–0.712 | ww | 0.3835–0.3875 | S |
| 0.667–0.676 | w | 0.3805–0.3845 | mS |
| 0.633–0.640 | w | 0.3780–0.3820 | mS |
| 0.595–0.602 | mw | 0.3740–0.3780 | m |
| 0.590–0.596 | w | 0.3715–0.3755 | m |
| 0.570–0.576 | mw | 0.3710–0.3750 | m |
| 0.566–0.572 | w (shoulder) | 0.3650–0.3690 | w |
| 0.555–0.564 | w | 0.3615–0.3650 | w |
| 0.535–0.541 | w | 0.3480–0.3515 | ww (broad) |
| 0.532–0.538 | w | 0.3435–0.3470 | w |
| 0.511–0.516 | ww (broad) | 0.3415–0.3450 | w |
| 0.502–0.506 | ww | 0.3385–0.3422 | ww |
| 0.496–0.501 | mw | 0.3342–0.3377 | w (broad) |
| 0.486–0.491 | ww (boad) | 0.3295–0.3329 | w |
| 0.469–0.474 | ww | 0.3245–0.3279 | w |

The germanozeosilite used as a catalyst in the process of the invention may be produced in the following manner:

(i) first preparing a reaction mixture, in an aqueous medium, containing at least one source of silicon having an oxidation state of +4, a source of germanium having an oxidation state of +4 and a structuring agent;

(ii) next crystallizing such reaction mixture by heating and recovering the crystallized precipitate therefrom; and (iii) then calcining said precipitate at a temperature above 450° C. to remove the structuring agent occluded in the channels of the zeolite.

In the case of a pH higher than approximately 12, the mobilizing agent comprises $OH^-$ ions. In the case of a pH below or equal to approximately 12, $F^-$ ions are added as a mobilizing agent.

In general, it is advisable to avoid the presence, in the reaction mixture, of alkali metal or ammonium ($NH_4^+$) cations, which form insoluble germanium compounds such as, for example, $KH_3GE_2O_6$, $NH_4H_3Ge_2O_6$, $Na_2Ge_3O_7\cdot 7H_2O$, $K_3HGe_7O_{16}\cdot xH_2O$ and $K_4Ge_9O_{20}$, and which block the germanium, preventing or limiting its incorporation into the germanozeosilite structure.

Many sources of silicon in an oxidation state of +4 may be employed in the process of the invention. Examples of which are silicas in the form of hydrogels, aerogels, xerogels and colloidal suspensions, the silicas resulting from precipitation from solutions of soluble silicates or from the hydrolysis of silicic esters such as $Si(OC_2H_5)_4$, and silicas prepared by extraction and activation treatments of natural or synthetic crystalline or amorphous compounds such as aluminum silicates, aluminosilicates and clays. Hydrolyzable tetravalent silicon compounds such as silicon halides or the like may also be used.

Exemplary sources of germanium in an oxidation state of +4 are $GeO_2$ oxide of the quartz type, and germanium compounds which can be hydrolyzed, such as alkoxides, halides or the like.

It is also possible to use compounds containing the elements silicon and germanium in combination such as, for example, glasses or mixed gels.

The sources of the elements silicon and germanium having a degree of oxidation of +4 may be introduced in the form of solutions, or as pulverulent solids, but also in the form of agglomerates such as, for example, pellets or extrudates, which can be converted into germanozeosilite without any change in shape.

The $OH^-$ mobilizing agent is introduced in the form of weak and/or strong base(s), preferably containing no alkali metal or $NH_4^+$ cations. Amines and quaternary ammonium hydroxides are thus illustrative.

The $F^-$ mobilizing agent is introduced in the form of acid and/or of salt(s) containing no alkali metal or $NH_4^+$ cations, and/or of compounds liberating $F^-$ when hydrolyzed. Exemplary such compounds are hydrofluoric acid, amine hydrofluorides, quaternary ammonium fluorides, $SiF_4$ and $GeF_4$.

Exemplary structuring agents which are suitable for use according to the invention are:

(a) the amines of formula (III):

in which $R_1$, $R_2$ and $R_3$, which may be identical or different, are each an alkyl radical, preferably a propyl or butyl radical;

(b) quaternary ammonium alkyl compounds of the formula (IV):

in which $R_1$, $R_2$, $R_3$ and $R_4$, which may be identical or different, are each alkyl radicals, preferably propyl or butyl radicals; and (c) compounds of the formulae (III) and (IV) in which the nitrogen has been replaced by a phosphorus atom.

The structuring agents are preferably compounds which can provide tetrapropylammonium or tripropylammonium cations.

The structuring agent can be introduced in the form of a base or of a salt, depending on the nature of the mobilizing agent(s) selected, and which will determine the pH range of the reaction mixture.

Thus, in the absence of $F^-$ anion, the high pH required for the synthesis can be attained by the introduction of the structuring agent in the form of a quaternary ammonium hydroxide of formula (IV). On the other hand, in the presence of $F^-$ anions, the structuring agent can be introduced in the form of a quaternary ammonium salt of formula (IV), or of the amine of formula (III), the pH being adjusted, if appropriate, by means of a base. This base will advantageously have the properties of a weak structuring agent in order not to compete with the structuring agent added. Thus, for example, the bases which are suitable per the invention are methylamine, dimethylamine, trimethylamine, ethylamine, diethylamine and triethylamine.

The reaction mixture advantageously has the following composition, expressed as a molar ratio:

Ge/(Si+Ge) ranging from 0.001 to 0.80; preferably, when the pH is higher than 12, ranging from 0.002 to 0.8, more preferably ranging from 0.01 to 0.7;and, when the pH is below or equal to 12, ranging from 0.001 to 0 75, preferably ranging from 0.002 to 0.60;

Structuring agent/(Si+Ge) ranging from 0.002 to 4, preferably ranging from 0.06 to 2 in the case of a pH higher than 12 and ranging from 0.06 to 1 in the case of a pH below or equal to 12;

F/(Si+Ge) ranging from 0.04 to 4, preferably ranging from 0.06 to 2 in the case of a pH below or equal to 12;and H$_2$O/(Si+Ge) ranging from 4 to 400, preferably ranging from 10 to 200 in the case of a pH higher than 12, and ranging from 20 to 200 in the case of a pH below or equal to 12.

When a base is employed to adjust the pH, the molar ratio of the base relative to (Ge+Si) ranges from greater than 0 to 12, and preferably ranges from 2 to 8.

The addition of crystal nuclei (seed crystals) of a specified structure, for example MFI, to this reaction mixture, in a proportion which does not exceed a few percent by weight relative to the weight of SiO$_2$ +GeO$_2$ introduced, can promote the crystallization of the germanozeosilite.

The crystallization of the germanozeosilite may be carried out by heating the reaction mixture to a temperature of from approximately 40° C. to approximately 240° C., preferably from 60° C. to 220° C., for that period of time required for crystallization, according to conventional operating procedure in the art of synthesis of zeolites. For example, such heating time may range from about 6 hours to about 500 hours.

This heating and crystallization are preferably carried out in a container or autoclave lined with a layer of, for example, polytetrafluoroethylene.

The reaction mixture may be stirred or unstirred.

After crystallization, the resulting precipitate is collected, for example, by filtration.

This precipitate is then heated, after drying, if desired, to a temperature above 450° C., preferably above 500 C, in order to decompose by calcination or thermal decomposition the organic species present in the precipitate, such as, for example, the structuring agent.

The phenols and phenol ethers which are the preferred starting materials in the process of the invention are the compounds of formula (I) in which R$_5$ is a hydrogen atom, a methyl radical or an ethyl radical, and R$_6$ is a hydrogen atom, a methyl, ethyl or tert-butyl radical or a methoxy or ethoxy radical.

Exemplary thereof are, without limitation, phenol, anisole, ortho-cresol, meta-cresol, para-cresol, 4-tert-butylphenol, 2-methoxyphenol and 4-methoxyphenol.

The process according to the invention is particularly applicable to phenol, for the preparation of hydroquinone and of pyrocatechol.

The hydrogen peroxide may be employed in the form of an aqueous solution which typically has a hydrogen peroxide concentration higher than 20% by weight. Hydrogen peroxide may also be employed in the form of a solution in an organic solvent. Exemplary organic solvents for such application of the hydrogen peroxide are the esters, especially the alkyl or cycloalkyl esters of saturated aliphatic carboxylic acids; the alkyl acetates and propionates containing from 4 to 8 total carbon atoms or mixtures of such esters are preferably employed. It is also possible to employ solutions of hydrogen peroxide in an ether, such as, for example, dioxane, diisopropyl ether or methyl tert-butyl ether.

The molar ratio of the compound of formula (I)/hydrogen peroxide typically ranges from 25/1 to 3/1 and preferably from 20/1 to 4/1.

The amount of germanozeosilite, described above, which can be used in the process of the invention may vary over very wide limits.

When the process is carried out noncontinuously, the catalyst may represent from 0.1% to 20% by weight, relative to the weight of the compound of formula (I) employed. This weight ratio will preferably range from 0.5% to 10%. However, when the process is carried out continuously, for example by reacting a mixture of compound (I) with a hydrogen peroxide solution in a fixed catalyst bed, these catalyst/compound (I) ratios are no longer meaningful and, at any given time, it will be possible to have a weight excess of catalyst relative to the compound (I).

It is also possible to carry out the hydroxylation of compound (I) in a solvent for the compound (I), which is preferably miscible or partially miscible in water.

Exemplary such solvents are water, alcohols such as methanol, tert-butanol, isopropanol or ethanol, ketones such as acetone or methyl isobutyl ketone, nitriles such as acetonitrile, carboxylic acids such as acetic acid, esters such as propyl acetate, ethers such as methyl tert-butyl ether, polar aprotic solvents such as tetrahydrothiophene dioxide (sulfolane), ethylene carbonate, propylene carbonate and N-methylpyrrolidone.

The temperature at which the reaction is conducted typically ranges from 45° to 160° C. at atmospheric pressure. It is also possible to operate at higher temperatures and at pressures above atmospheric pressure.

In order to further illustrate the present invention and the advantages thereof, the following specific examples are given, it being understood that same are intended only as illustrative and in nowise limitative.

EXAMPLE 1

Preparation of Catalysts (1a) and (1b)

Catalyst (1a)

This example describes synthesis of a zeolite in an acidic medium, using F$^-$ ions as a mobilizing agent.

A solution A and a xerogel were prepared

Solution A

This was obtained by mixing tri-n-propylamine, HF and tetrapropylammonium bromide (TPA-Br): 4 g of 50% aqueous HF were diluted in 25 cm$^3$ of water, and 7.15 g of tri-n-propylamine were added thereto, under stirring. The stirring was continued until a single liquid phase was obtained, and 6.65 g of TPA-Br were then added, dissolved in 27 cm$^3$ of water.

Xerogel 17 g of SiCl$_4$ and 2.15 g of GeCl were mixed, under stirring, in 20 cm$^3$ of n-propanol, and 60 g of water were then added dropwise. A gel was produced, which was dried at 80° C. until a product weight equal to 10.4 g was obtained.

This gel was slowly dispersed in solution A, under stirring.

This mixture had the following composition (expressed per 1 mole of SiO$_2$): 0.25 TPA-Br; 0.5 tri-n-propylamine; 1 HF; 1 SiCl$_4$; 0.1 GeCl$_4$; 30 H$_2$O.

0.12 g of ground crystals which had a structure of the MFI type were dispersed in this mixture, as crystallization nuclei. The reaction mixture, characterized by a pH of 1.5, was heated for two weeks at 96° C. After separation of the mother liquors, copious washing with water and drying in the oven at 80° C., 4.5 g of crystals containing a few amorphous particles were obtained. These were calcined for 6 hours in air at 550° C.

The X-ray diffraction pattern obtained from the calcined product was consistent with the values reported in the above Table. The final product germanozeosilite had the formula:

$(Si_{91.3}Ge_{4.7})O_{192}$ and it additionally contained 0.6% (by weight) of fluorine.

Catalyst 1(b)

A solution A and a solution B were first prepared

Solution A 6.432 g of GeCl$_4$ were poured dropwise into 1.4 cm$^3$ of a 50% aqueous solution of HF.

Solution B 5.326 g of TPA-Br were dissolved in 36 g of water and 21.742 g of a 40% solution of CH$_3$NH$_2$ in water were then introduced.

Solution B was added dropwise into solution A, under stirring.

A white precipitate formed. Stirring was continued for 15 minutes.

0.060 g of very finely ground crystals which had a structure of MFI type were dispersed in this mixture as crystallization nuclei, together with 3.00 g of SiO$_2$ (in the form of Aerosil).

Stirring was carried out for 30 minutes.

The pH of the mixture was 12–12.5.

This mixture had the following composition: 1.25 SiO$_2$; 0.5 TPA-Br; 7 CH$_3$NH$_2$; 1 HF; 0.75 GeCl$_4$; 50 H$_2$O.

It was transferred into a 100-cm$^3$ cylindrical container made of Teflon, placed in a metal autoclave.

After the autoclave was closed, the assembly was heated for 15 minutes to 180 to 190° C.

After reaction and cooling, the pH was 12.

The product was filtered, washed copiously with water and dried in the oven at 80° C. A total mass of approximately 4.3 g was obtained, containing a few amorphous particles. It was then calcined for 6 hours in air, at 550° C.

The X-ray diffraction pattern obtained from the calcined product was consistent with the values reported in the above Table. The final product germanozeosilite had the formula:

$(Si_{81}Ge_{15})O_{192}$

EXAMPLE 2

The following materials were charged into a 30-cm$^3$ Pyrex glass reactor fitted with a central bar-magnet stirrer, a condenser connected to a gas flowmeter, a controlled heating system and an injection system, after the apparatus had first been purged with nitrogen:

(i) 4.7 g of phenol (0.05 mol);
(ii) 0.25 g of germanozeosilite prepared as in Example (1a);
(iii) 4.8 g of distilled water.

The mixture was heated to 100° C. under stirring and then an aqueous solution of H$_2$O$_2$, at a concentration of 70% by weight/volume, was injected therein (0.0025 mol of H$_2$O$_2$).

The reaction was then permitted to proceed for 2 hours, 30 minutes.

After the catalyst had been filtered off, the unconverted H$_2$O$_2$ was determined by iodometry and the diphenols by high performance liquid chromatography (HPLC).

The following results were obtained:

| | | |
|---|---|---|
| (a) | Degree of conversion (DC) of H$_2$O$_2$ | 97.0% |
| (b) | Yield of pyrocatechol based on H$_2$O$_2$ converted (CY) | 35.0% |
| (c) | Yield of hydroquinone based on H$_2$O$_2$ converted (CY) | 24.5% |
| (d) | Total yield of diphenols | 59.5% |

EXAMPLE 3

The procedure of Example 2 was repeated using the same amounts of reactants and under the same operating conditions, but employing the germanozeosilite prepared in Example (1b).

| | | |
|---|---|---|
| (a) | Degree of conversion (DC) of H$_2$O$_2$ | 93.0% |
| (b) | Yield of pyrocatechol based on H$_2$O$_2$ converted (CY) | 13.5% |
| (c) | Yield of hydroquinone based on H$_2$O$_2$ converted (CY) | 9.0% |
| (d) | Total yield of diphenols | 22.5% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the hydroxylation of a phenol or phenol ether, comprising reacting a compound comprising formula (I):

in which R$_5$ is a hydrogen atom, or a methyl, ethyl or phenyl radical, and R$_6$ is a hydrogen atom, an alkyl radical having from 1 to 4 carbon atoms, an alkoxy radical having from 1 to 4 carbon atoms, or a phenyl or cyclohexyl radical, with hydrogen peroxide, in the presence of a catalytically effective amount of a calcined germanozeosilite MFI zeolite.

2. The process as defined by claim 1, said calcined germanozeosilite MFI zeolite having the formula (II):

$Si_{(96-x)}Ge_xO_{192}$      (II)

wherein x is a value that ranges from about 0.1 to 36.

3. The process as defined by claim 2, wherein formula (I), R$_5$ is a hydrogen atom or a methyl or ethyl radical, and R$_6$ is a hydrogen atom, a methyl, ethyl or tert-butyl radical, or a methoxy or ethoxy radical.

4. The process as defined by claim 2, said compound of the formula (I) comprising phenol, anisole, ortho-cresol, meta-cresol, para-cresol, 4-tert-butylphenol, 2-methoxyphenol or 4-methoxyphenol.

5. The process as defined by claim 2, said calcined germanozeosilite MFI zeolite comprising from 0.01% to 1.4% by weight of fluorine.

6. The process as defined by claim 2, said calcined germanozeosilite MFI zeolite having been prepared by:
   (i) first producing a reaction mixture, in an aqueous medium comprising at least one silicon compound having an oxidation state of +4, a germanium compound having an oxidation state of +4 and a structuring agent;
   (ii) next crystallizing such reaction mixture by heating and recovering the crystallized precipitate therefrom; and
   (iii) then calcining said precipitate at a temperature above 450° C. to remove the structuring agent occluded in the channels of the zeolite.

7. The process as defined by claim 6, wherein the preparation of said germanozeosilite, the molar ratio Ge/(Si+Ge) in the reaction mixture ranges from 0.001 to 0.75 when the pH of said reaction mixture is less than or equal to 12.

8. The process as defined by claim 7, said molar ratio ranging from 0.002 to 0.60.

9. The process as defined by claim 6, wherein the preparation of said germanozeosilite, the molar ratio Ge/(Si+Ge) in the reaction mixture ranges from 0.001 to 0.80 when the pH of said reaction mixture is greater than 12.

10. The process as defined by claim 9, said molar ratio ranging from 0.01 to 0.70.

11. The process as defined by claim 7, wherein the preparation of said germanozeosilite, the molar ratio F/(Si+Ge) in the reaction mixture ranges from 0.06 to 2.

12. The process as defined by claim 9, wherein the preparation of said germanozeosilite, the molar ratio $H_2O$/(Si+Ge) in the reaction mixture ranges from 4 to 400.

13. The process as defined by claim 12, said molar ratio ranging from 10 to 200.

14. The process as defined by claim 7, wherein the preparation of said germanozeosilite, the molar ratio $H_2O$/(Si+Ge) in the reaction mixture ranges from 4 to 400.

15. The process as defined by claim 14, said molar ratio ranging from 10 to 200.

16. The process as defined by claim 9, wherein the preparation of said germanozeosilite, the molar ratio structuring agent/(Si+Ge) in the reaction mixture ranges from 0.002 to 4.

17. The process as defined by claim 16, said molar ratio ranging from 0.06 to 2.

18. The process as defined by claim 7, wherein the preparation of said germanozeosilite, the molar ratio structuring agent/(Si+Ge) in the reaction mixture ranges from 0.002 to 4.

19. The process as defined by claim 18, said molar ratio ranging from 0.06 to 1.

20. The process as defined by claim 1, wherein the molar ratio compound of formula (I)/hydrogen peroxide ranges from 25/1 to 3/1.

21. The process as defined by claim 20, said molar ratio ranging from 20/1 to 4/1.

22. The process as defined by claim 1, carried out noncontinuously and wherein the amount of said germanozeosilite ranges from 0.1% to 20% by weight of said compound of formula (I).

23. The process as defined by claim 22, wherein said amount ranges from 0.5% to 10%.

24. The process as defined by claim 1, carried out continuously in a fixed catalyst bed.

25. The process as defined by claim 1, said hydrogen peroxide comprising an aqueous solution thereof.

26. The process as defined by claim 1, said hydrogen peroxide comprising an organic solution thereof.

27. The process as defined by claim 1, carried out at a temperature of from 45° C. to 160° C.

28. The process as defined by claim 1, said hydroxylation reaction being carried out in a solvent for the compound of formula (I).

29. The process as defined by claim 28, said solvent comprising water, an alcohol, a ketone, a nitrile, a carboxylic acid, an ester, an ether, or a polar aprotic solvent.

30. The process as defined by claim 26, wherein said organic solvent is selected from the group consisting of esters, alkyl acetates, ethers, proprionates containing from 4 to 8 total carbon atoms or mixtures thereof.

* * * * *